(12) United States Patent
Tegg et al.

(10) Patent No.: US 10,335,574 B2
(45) Date of Patent: Jul. 2, 2019

(54) ACCELEROMETER-BASED CONTACT SENSING ASSEMBLY AND SYSTEM

(71) Applicant: St. Jude Medical, Atrial Fibrillation Division, Inc., St. Paul, MN (US)

(72) Inventors: Troy T. Tegg, Elk River, MN (US); Saurav Paul, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 15/723,413

(22) Filed: Oct. 3, 2017

(65) Prior Publication Data

US 2018/0104446 A1    Apr. 19, 2018

Related U.S. Application Data

(60) Division of application No. 13/740,624, filed on Jan. 14, 2013, now Pat. No. 9,814,860, which is a continuation of application No. 12/347,246, filed on Dec. 31, 2008, now Pat. No. 8,369,921.

(51) Int. Cl.
| | |
|---|---|
| *A61M 25/00* | (2006.01) |
| *A61B 5/06* | (2006.01) |
| *A61N 1/365* | (2006.01) |
| *A61B 34/20* | (2016.01) |
| *A61M 25/01* | (2006.01) |

(52) U.S. Cl.
CPC ......... *A61M 25/0054* (2013.01); *A61B 5/067* (2013.01); *A61N 1/36542* (2013.01); *A61N 1/36578* (2013.01); *A61B 2034/2048* (2016.02); *A61B 2562/0219* (2013.01); *A61M 25/00* (2013.01); *A61M 2025/0166* (2013.01)

(58) Field of Classification Search
CPC   A61N 1/36578; A61N 1/36542; A61B 5/067; A61B 2562/0219; A16B 2034/2048
USPC ..................................... 606/32–50
See application file for complete search history.

(56) References Cited

U.S. PATENT DOCUMENTS

| | | | |
|---|---|---|---|
| 5,304,208 A * | 4/1994 | Inguaggiato | ......... A61N 1/0565 607/122 |
| 5,628,777 A | 5/1997 | Moberg et al. | |
| 7,263,397 B2 | 8/2007 | Hauck et al. | |
| 8,369,921 B2 | 2/2013 | Tegg et al. | |
| 2003/0045805 A1 | 3/2003 | Sheldon et al. | |
| 2004/0116901 A1* | 6/2004 | Appling | ................... A61L 29/18 604/523 |
| 2007/0156019 A1* | 7/2007 | Larkin | ................... B25J 19/025 600/104 |
| 2008/0027385 A1* | 1/2008 | Freeman | .............. A61B 5/1411 604/117 |

* cited by examiner

*Primary Examiner* — Nathan R Price
*Assistant Examiner* — Anh Bui
(74) *Attorney, Agent, or Firm* — Dykema Gossett PLLC

(57) ABSTRACT

A catheter system including an accelerometer-based sensing assembly is provided. In particular the present teachings relate to an accelerometer based assembly used to determine contact between a catheter and surrounding proximate tissue, such as cardiac tissue. An embodiment of such a system may, for example, be used for visualization, mapping, ablation, or other methods of diagnosis and treatment of tissue and/or surrounding areas.

19 Claims, 6 Drawing Sheets

ACCELEROMETER-BASED CONTACT SENSING ASSEMBLY AND SYSTEM

CROSS-REFERENCE TO RELATED APPLICATIONS

This application is a division of U.S. application Ser. No. 13/740,624 (the '624 application), filed 14 Jan. 2013, now pending, which is a continuation of U.S. application Ser. No. 12/347,246, filed 31 Dec. 2008 (the '246 application), now U.S. Pat. No. 8,369,921. The '624 application and the '246 application are hereby incorporated by reference as though fully set forth herein.

BACKGROUND OF THE INVENTION a. Field of the Invention

The present disclosure relates to an accelerometer-based assembly for detecting electrode contact with tissue.

b. Background Art

Electrophysiology catheters are used for an ever-growing number of procedures. For example, catheters have been used for diagnostic, therapeutic, mapping and ablative procedures, to name just a few examples. Typically, a catheter is manipulated through the patient's vasculature and to the intended site, for example, a site within the patient's heart, and carries one or more electrodes, which may be used for mapping, ablation, diagnosis, or other treatments.

Techniques of mapping, visualization and treatment using energizing sources, such as radio frequency (RF) ablation, often rely on the placing of an electrode in consistent mechanical contact with targeted tissue. In particular, lesion formation (such as lesions created by exposure to radio frequency), partially depends upon the adequacy of contact between the electrode and tissue. However, there are some challenges. For endocardial applications, the point of electrode-tissue contact is typically 150 cm away from the point of application of force applied by the operator of the catheter outside of the body. This distance complicates making and maintaining good contact between the electrode and tissue. Moreover, the absolute distance, when coupled with the fact that a beating heart is a dynamically moving wall, gives rise to some functional and theoretical challenges, such as ensuring that the electrode is in constant or near-constant mechanical contact with the myocardial wall, or as needed for effective lesion formation.

Catheter systems having sensor assemblies, such as those mounted on the catheter shaft proximal to the electrode or those mounted remotely in the handle set, leave the possibility, albeit a very small one, of obtaining false positive readings of contact between the electrode and the tissue. Such false positive outcomes may occur, for example, when the catheter wall, and not the electrode, is in contact with the tissue. Such a condition may arise during catheter manipulation in the heart when, for instance, the distal portion of the catheter is curled inwards so much as to lose electrode contact with the tissue, while the distal portion of the catheter is in contact with the tissue. When that happens, remotely placed sensors generate signals due to the deflection of the catheter shaft, thereby falsely indicating contact between the electrode and tissue.

Additionally, current force sensing methods may be sensitive to thermal changes at an electrode, such as during an ablation procedure. This may lead to incorrect readings of electrode interaction with surrounding tissue.

There is thus a need for a system and method that minimizes one or more problems as described above.

BRIEF SUMMARY OF THE INVENTION

Systems and methods are provided for measuring acceleration of an electrode coupled to a medical device, such as a catheter. Measured acceleration of an electrode may be used to determine forces acting on the electrode, and to determine when the electrode is in contact with tissue. The systems described herein may substantially reduce, or eliminate, false positive readings of electrode contact with tissue.

One or more accelerometers are coupled to an electrode. Signals received from the one or more accelerometers are used to determine either or both of the magnitude and the direction of the acceleration of the electrode. When multiple accelerometers are coupled to the electrode, they may be used in concert with each other to determine acceleration vectors of the electrode. In an embodiment, the force acting on the electrode may be determined from the acceleration of the electrode. For example, the electrode may have a known mass, so the force may be derived by a processor configured to multiply the mass by the acceleration, since Force (F)=Mass (m)×Acceleration (a), i.e. F=ma. Force may also be determined using a lookup table or the like which may be provided in advance for a particular electrode based on the electrode mass, to directly translate acceleration signals into a force indicative parameter.

An accelerometer may be coupled directly to an electrode, or may be coupled to a carrier disposed between the accelerometer and the electrode. For example, in an embodiment, one or more accelerometers may be coupled directly to a base of an electrode. In such an embodiment, accelerometers are displaced when electrodes are displaced, and the accelerometers thus directly measure electrode acceleration. In another embodiment, accelerometers are coupled to a carrier which is mated to the electrode. In such an embodiment, when forces cause an acceleration of the electrode, forces are transmitted through the carrier. The transmitted forces cause accelerometers to be displaced, or to accelerate. The signals output from the accelerometers can then be used to determine the acceleration of the electrode which caused the acceleration of the accelerometer. This may in turn be used to determine forces acting on the electrode. When the accelerometer is coupled directly to the electrode, a thermally insensitive accelerometer may be used to minimize effects of electrode heat. When accelerometers are separated from an electrode by a carrier, the carrier may be configured to provide a thermally insulative effect, protecting the accelerometer from heat.

Carriers may take any of a variety of forms. In one embodiment, a carrier may resemble a tripod, having a plurality of legs extending from a central body, where the electrode is mounted to the central body, and accelerometers are mounted to each of the legs. When such an electrode moves, there may be a corresponding movement of the legs. In another embodiment, the carrier may have a cylindrical body with a diaphragm provided across an end. A lever may be attached to the diaphragm, at one end, and to the electrode at the other end, thereby connecting the two. Accelerometers may be mounted on the diaphragm. When a force acts on the electrode, the lever may be moved, transferring the force to the diaphragm. The accelerometers may be configured to measure the acceleration of the diaphragm, and this acceleration may be used to determine the acceleration of the electrode.

When forces acting on the electrode are determined, they may be analyzed to determine whether the forces are indicative of electrode contact with tissue. This determination may be made in a number of ways. For example, forces acting on an electrode may be compared to forces acting on, e.g., a catheter shaft. If the force acting on the electrode is greater than the force acting on the shaft, this may indicate that the electrode is in contact with tissue. Acceleration may also be compared with the frequency of a heart beat, to determine if accelerations are contemporaneous with the systole and diastole of a cardiac chamber.

Forces acting on the electrode may also be used for other purposes, such as determining the health of tissue in a particular area. For example, when contact is made between an electrode and heart tissue, the magnitude of the force imparted on the electrode may be indicative of the strength and the health of the tissue.

In an embodiment, an receiver or controller responsive to the accelerometer signals is configured to indicate to a user at least one of a number of defined parameters, such as (1) an electrode acceleration, (2) a force acting on an electrode, and (3) a degree of electrode-to-tissue contact. The indication may be made using one or more indicators, such as a screen or other visual cue. Additionally, or alternatively, the user (e.g., an electrophysiologist—EP) may be notified only when an electrode is not accelerating, or is no longer in contact with tissue.

Systems such as those described above may be used during procedures, such as surgical procedures, therapeutic or diagnostic procedures, in many ways. In one embodiment, systems of the invention may be used to ensure ablation electrodes remain in contact with target tissue throughout an ablation procedure. In an embodiment, such systems may be used to determine the force with which heart muscle can repel an electrode, which may be an indicator of the local strength of cardiac tissue, and may be useful in diagnosing heart health. Other methods and uses for the present teachings are also contemplated.

DETAILED DESCRIPTION OF THE INVENTION

Figure 1:
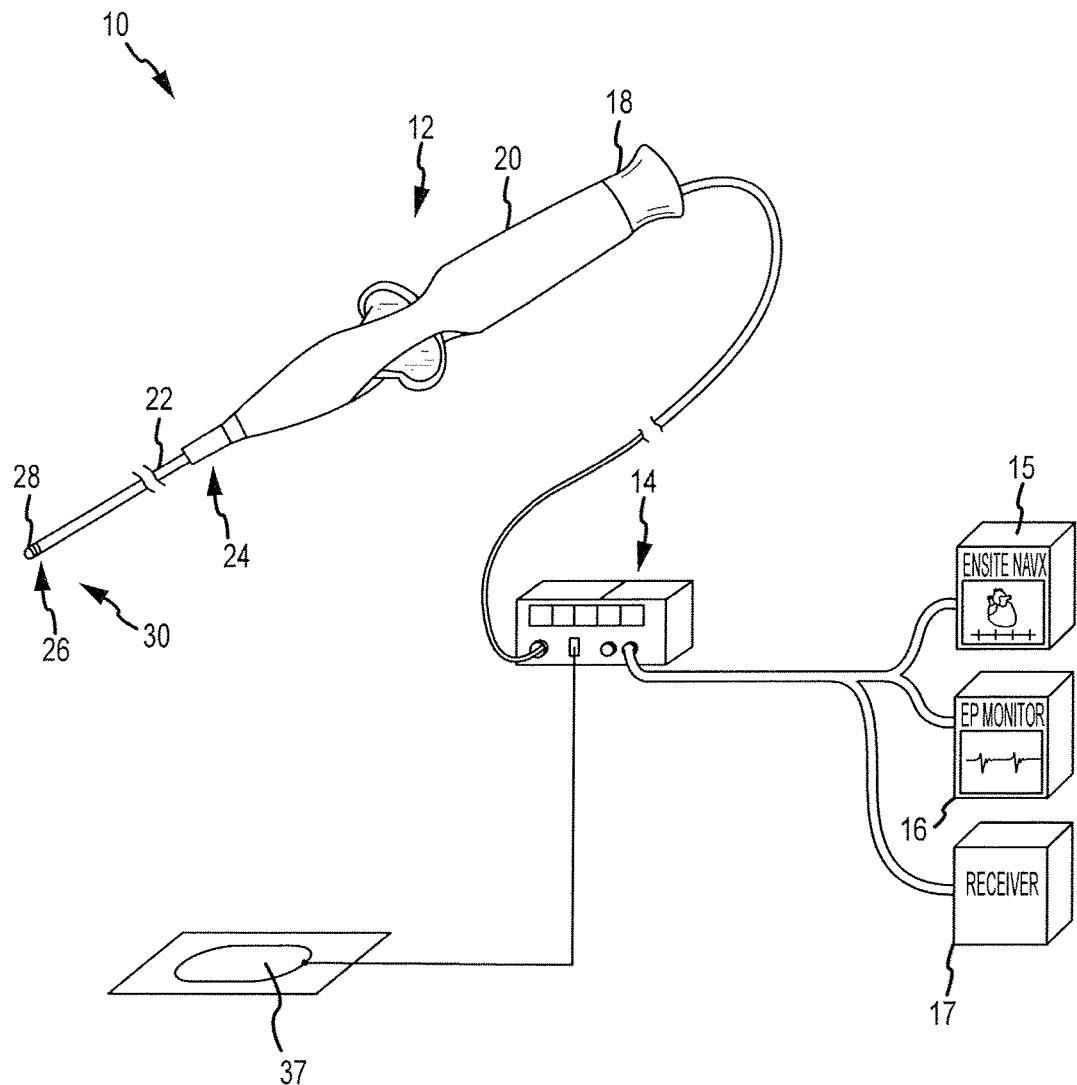
FIG. 1 is a perspective view of a catheter in accordance with an embodiment.

Referring now to the drawings, wherein like reference numerals are used to identify like components in the various views, FIG. 1 is a simplified, perspective view of a system 10 for conducting a diagnostic or therapeutic function, which also includes a capability for measuring electrode acceleration.

The illustrated system 10 includes a catheter 12 operably connected to a controller 14, which may be an energy source. By way of example, and not of limitation, the catheter 12 may be an RF ablation catheter, and the controller 14 may be an RF ablation generator. Controller 14 may be configured to facilitate the operation of catheter 12, such as during ablation procedures, and may involve monitoring any number of chosen variables (e.g., temperature of an ablation electrode, ablation energy), and providing a requisite energy source. Additional components, such as visualization, mapping, and navigation components, may also be integrated into the system 10. For example, an EnSite Electro Anatomical Mapping System 15, commercially available from St. Jude Medical, Inc., and as also seen generally by reference to U.S. Pat. No. 7,263,397 entitled "Method and Apparatus for Catheter Navigation and Location and Mapping in the Heart" to Hauck et al., owned by the common assignee of the present invention, and hereby incorporated herein by reference in its entirety. Additionally, an electrophysiological monitor or display, such as an electrogram signal display 16, or other system, may also be integrated into the system 10.

Catheter 12 may include a cable connector portion or interface 18, a handle 20, and a shaft 22 having a proximal end 24 and a distal end 26. In the illustrated embodiment, an electrode 28 is disposed on the shaft 22, near the distal end 26. Though not illustrated in FIG. 1, the stiffness of distal end 26 may be non-uniform along the length thereof. For instance, distal end 26 may include an outermost portion (i.e., axially most remote from the handle) which may have a relative stiffness that is less than the stiffness of contiguous but more proximal areas of the distal end 26. In an embodiment, forces applied to a shaft 22 may not translate to an electrode 28 coupled to the flexible outermost portion, or may be attenuated at least in part by the relatively flexible outermost portion. Shaft 22 may further include one or more additional electrodes (not pictured), such as ring electrodes, configured for intra-cardiac use. One or more electrodes, such as electrode 28, may be used for any number of diagnostic and/or therapeutic purposes including, but not limited to, RF ablation, cardiac mapping, electrophysiological studies, and other procedures. Accordingly, the present disclosure is not limited to any one type of catheter or catheter-based system or procedure. Moreover, it should be understood that embodiments consistent with the present invention may include features not shown or described herein for the sake of brevity and clarity. For example, an ablation catheter may typically include additional electrodes (and corresponding leads), a temperature sensor (and corresponding leads), and other features, as known.

Catheter 12, and controller 14, may include structures and functions common to known catheter systems. For example, controller 14 may comprise conventional RF ablation apparatus, such as a commercially available unit sold under the model number IBI-1500T RF Cardiac Ablation Generator, available from Irvine Biomedical, Inc. Of course, controller 14 may also comprise various other known energy sources. In an ablation embodiment, controller 14 may include an ablation generator. In such an embodiment, electrode 28 may be configured to receive excitation energy from the ablation generator, and to output ablation energy to tissue within a treatment area, such as to heart tissue within a cardiac chamber. In such an embodiment, a patch 37 may be provided, which may act as an electrical return for an RF ablation signal. The patch 37 is formed of electrically conductive material to form an electrode, and is configured for affixation to the body of a patient.

One or more accelerometers 30 (as generally shown in FIG. 1) may be coupled to the electrode 28 within the catheter shaft 22. The accelerometer 30 may include one or more wires, which may be configured to provide power to the accelerometer 30 and/or to carry a signal indicative of sensed acceleration. Acceleration signals may be provided to a suitable receiver, such as a receiver 17. Receiver 17 may be configured to receive signals from one or more devices within, or in communication with, catheter 12. Receiver 17 may include, or may be in communication with, one or more logic systems configured to receive and analyze the received signals. Receiver 17 may be configured to receive a signal from accelerometer 30, and to determine the acceleration of electrode 28, or other parameters as will be described in detail below. For example, receiver 17 may also be configured to determine the force acting on the electrode 28. Force acting on the electrode may be determined by, for example, multiplying the acceleration of the electrode 28 by the mass of the electrode 28, or by referencing a look-up table. In an embodiment, system 10 may include a plurality of accelerometers 30 coupled to electrode 28. Receiver 17 may be configured to receive respective acceleration signals from each of the accelerometers 30, and to determine a vector representative of the magnitude and direction of the acceleration of electrode 28. Receiver 17 may be further configured to determine a corresponding force vector acting on the electrode 28. The receiver may be a standalone unit, as illustrated in FIG. 1. Receiver may also be incorporated with another piece of equipment, such as controller 14, EnSite NavX system 15, etc.

Accelerometer 30 may be any type of accelerometer 30 and may further take many different forms. By way of example, and not of limitation, accelerometer may be a piezoelectric sensor, a piezoresistive sensor, a capacitive sensor, an electromechanical sensor, a micro-electromechanical system, a nano-electromechanical system, a low impedance output field effect transistor, a strain-gauge, a magnetic induction sensor, an L-C tank sensor, an optical sensor, a laser sensor, or combinations thereof.

Figure 2:
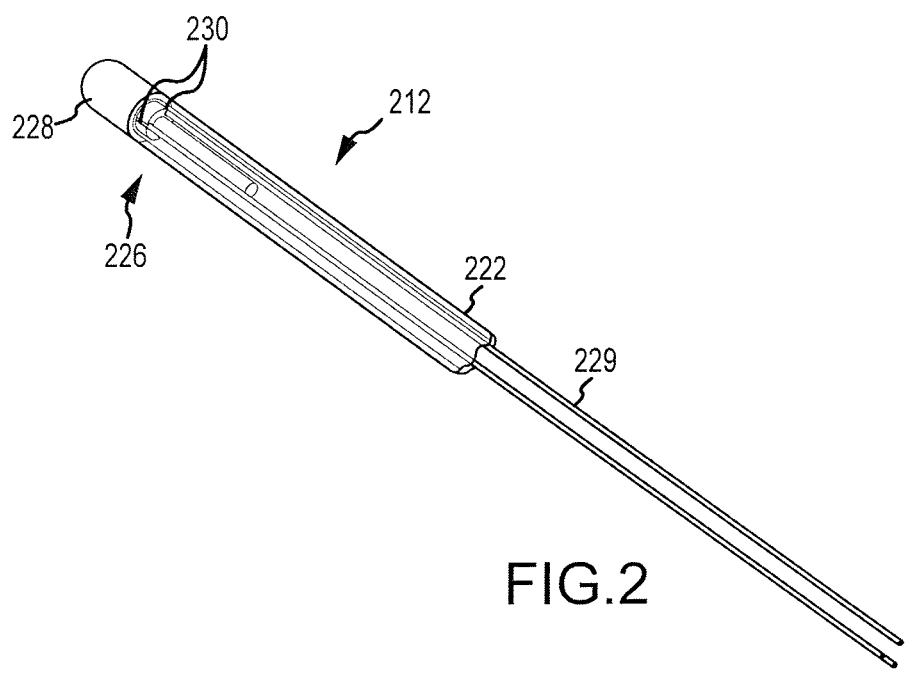
FIG. 2 is a partial perspective view of the catheter of FIG. 1.

FIG. 2 is a partial section view of a shaft 222 of a catheter 212, according to an embodiment. Catheter 212 may be similar to catheter 12 illustrated in FIG. 1. An electrode 228 is coupled to a distal end 226 of catheter shaft 222. An accelerometer 230 (not illustrated) may be coupled to a proximal end of electrode 228. When forces act on electrode 228, and electrode 228 is displaced, accelerometer 230 is similarly displaced. When displaced, accelerometer 230 may be configured to provide a signal indicative of the acceleration of electrode 228 to a receiver, such as receiver 17 (best shown in FIG. 1). The receiver 17 may be configured to receive the acceleration signals, and to determine at least one of the magnitude and direction of the acceleration of electrode 228. Accelerometer 230 may transmit signals to receiver 17 along a wire, such as wire 229.

Figure 3:
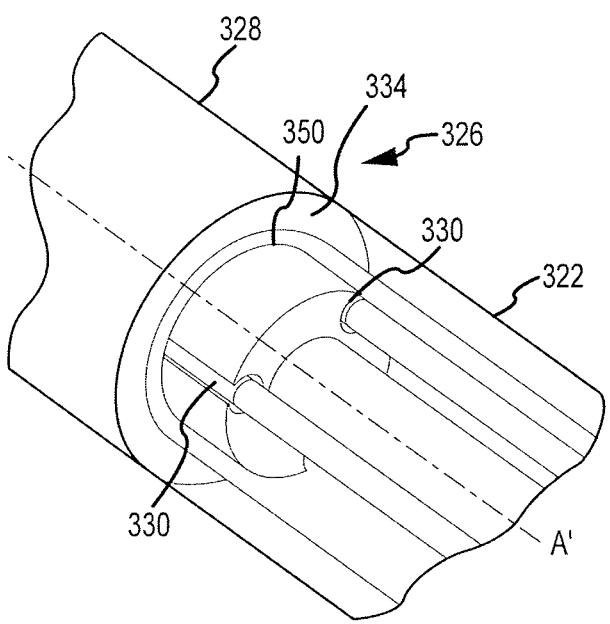
FIG. 3 is an enlarged partial perspective view of the catheter of FIG. 1, showing an electrode assembly in accordance with an embodiment.

FIG. 3 is a partial perspective view of an electrode 328, which may be similar to electrode 228 illustrated in FIG. 2. Electrode 328 is coupled to the distal end 326 of the shaft 322 of a catheter. Electrode 328 includes a proximal portion 334 defining a lumen 350. Lumen 350 may be centered about an axis A' defined through the center of electrode 328. One or more accelerometers 330 may be coupled to electrode 328. For example, in the illustrated embodiment, three accelerometers 330 are coupled to the electrode 328 along proximal portion 334. The three accelerometers 330 may be equally spaced circumferentially around axis A' defined through the center of lumen 350 and may all be positioned approximately the same radial distance from axis A. Accelerometers 330 may each be configured to provide a respective acceleration signal to a receiver, such as receiver 17, when electrode 328 is subjected to an external force. An external force may be, for example, force from a beating heart with which an electrode 328 is in contact. Receiver 17 may be configured to receive the acceleration signals from accelerometers 330, and to determine a vector representative of the acceleration of electrode 328. As described previously, receiver 17 may further be configured to determine forces acting on electrode 328, and to determine whether electrode 328 is in contact with tissue.

Figure 4:
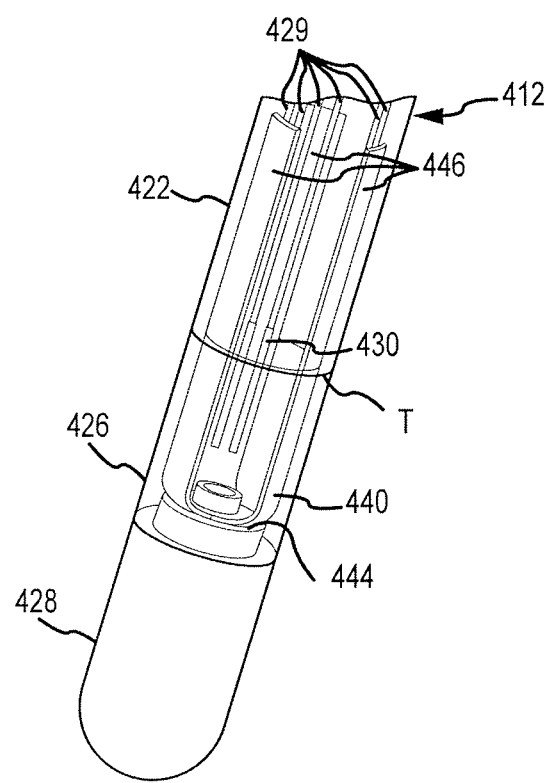
FIG. 4 is an enlarged perspective view of an alternate embodiment of an electrode assembly.

FIG. 4 is a partial perspective view of an alternate embodiment of the invention, designated catheter 412. Catheter 412 includes an electrode 428. Electrode 428 is coupled to the distal end of a support structure 440. Support structure 440 is housed within a distal end 426 of a catheter 412. Distal end 426 of catheter 412, which may include the portions of catheter 412 distal of line T, may be more flexible than the rest of catheter 412, allowing for greater mobility of electrode 428.

The support structure 440 includes a distal base 442 having a outer surface 444 to which electrode 428 is coupled. Support structure 440 further includes a plurality of proximally directed protrusions 446. Protrusions 446 are anchored to shaft 422 of catheter 412. In an embodiment, protrusions 446 may traverse flexible distal end 426 and may be anchored to shaft 422 at a point proximal to line T. Protrusions 446 may be equally spaced circumferentially about support structure 440. One or more accelerometers 430 may be coupled to one or more of protrusions 446. In the illustrated embodiment, three accelerometers 430 may be included, each coupled to a respective protrusion 446.

When a force is applied to electrode 428, such as the force of a beating heart, electrode 428 is displaced. The displacement of electrode 428 may be resolved across the support structure 440, causing a respective dynamic strain to be produced in one or more of the protrusions 446. Each accelerometers 430 coupled to a respective protrusions 446 generates an acceleration signal in response to the strain. Acceleration signals may then be transmitted from the one or more accelerometers 430 to a receiver, such as receiver 17, along wires 429. Received acceleration signals may then be used to determine the magnitude and/or direction of acceleration and/or orientation of electrode 428. Received signals may also be used to determine the force acting on electrode 428, and may be used to determine whether electrode 428 is in contact with an external body, such as a heart wall.

Protrusions 446 of FIG. 4 are generally illustrated as forming a tripod structure, and generally have an elongated shape. Protrusions may take any of a myriad of shapes, including a C-shape, a laterally inverted C-shape, a U-Shape, an inverted U-shape, an Omega ($\Omega$) shape, an inverted Omega shape, an L-shape, a coil shape, a transversely aligned coil, or any other suitable shape.

Figure 5A:
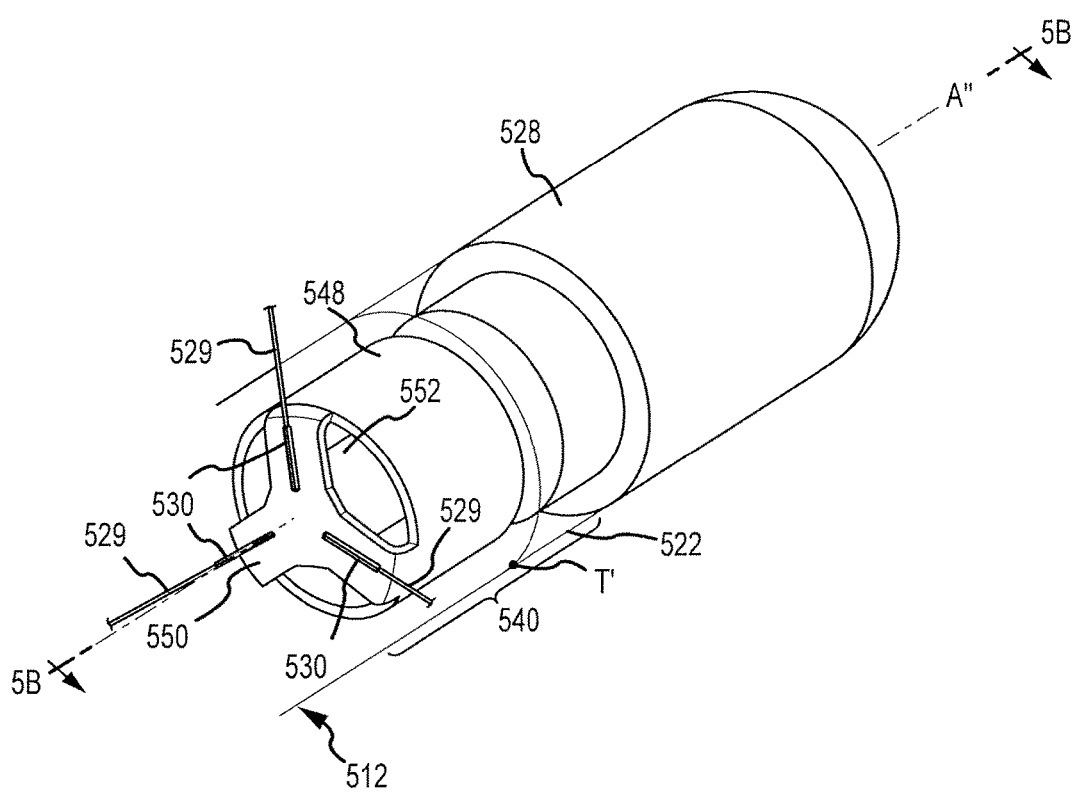
FIG. 5A is an enlarged perspective view of a further embodiment of an electrode assembly.

FIG. 5A is a partial perspective view, with portions broken away, of a further catheter embodiment of the invention, designated catheter 512, which includes an electrode 528. A support structure 540 includes a cylindrical base 548. A diaphragm 550 extends across at least a portion of an aperture defined by cylindrical base 548, and is coupled to base 548 at various locations. A lever 552 is positioned along an axis A" defined through the center of support structure 540. A proximal end of lever 552 may be coupled to a proximal face 553 (See FIG. 5B) of diaphragm 550. A distal end of lever 552 is coupled to electrode 528. One or more accelerometers 530 may be coupled to an outer face 555 of diaphragm 550.

Cylindrical base 548 may be configured to be coupled to a shaft of catheter 512. For example, base 548 may be coupled to shaft 522 at a point proximal to line T'. A proximal end of electrode 528 may be coupled to flexible distal end 522 of catheter 512. If a force is applied to electrode 528, electrode 528 may be displaced, causing a corresponding strain on diaphragm 550. Accelerometers 530 may detect the strain on diaphragm 550 and generate signals in response thereto. Signals may be transmitted to a receiver, such as receiver 17, along wires 529. Receiver 17 may process the received signals and determine acceleration of electrode 528, as well as forces acting on electrode 528. This information may then be used to determine electrode contact with tissue.

Figure 5B:
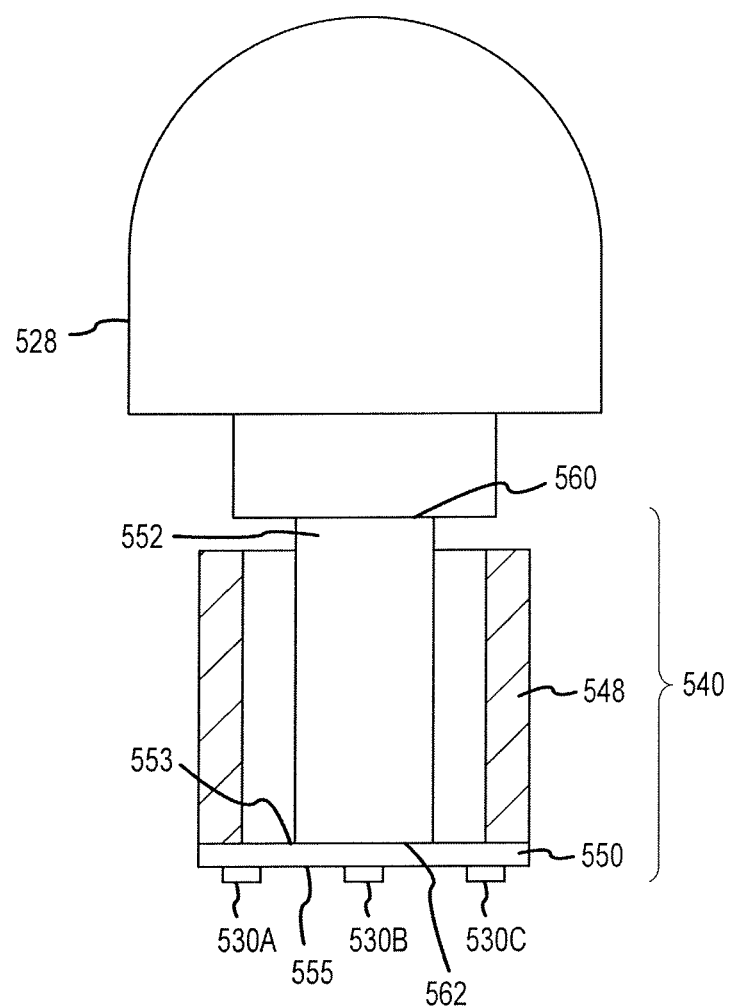
FIG. 5B is partial cross-sectional view of the electrode assembly of FIG. 5A taken substantially along line 5B-5B.

FIG. 5B is a partial cross-sectional view of electrode 528 and support structure 540 of FIG. 5A taken substantially along line 5B-5B. Lever 552 is coupled to electrode 528 at a proximal end 560, and to a proximal face 553 of diaphragm 550 at a distal end 562. Diaphragm 550 extends across a distal end of cylindrical base 548 of support structure 540. Lever 552 is configured to interact with electrode 528 and with proximal face 553 of diaphragm 550, such that displacement of electrode 528 causes lever 552 to create a force against proximal face 553 of diaphragm 550. A plurality of accelerometers 530 are positioned along a distal face 555 of diaphragm 550. Lever 552 is thus configured to transfer forces applied to electrode 528 to diaphragm 550, where they are detected by accelerometers 530.

Figure 6:
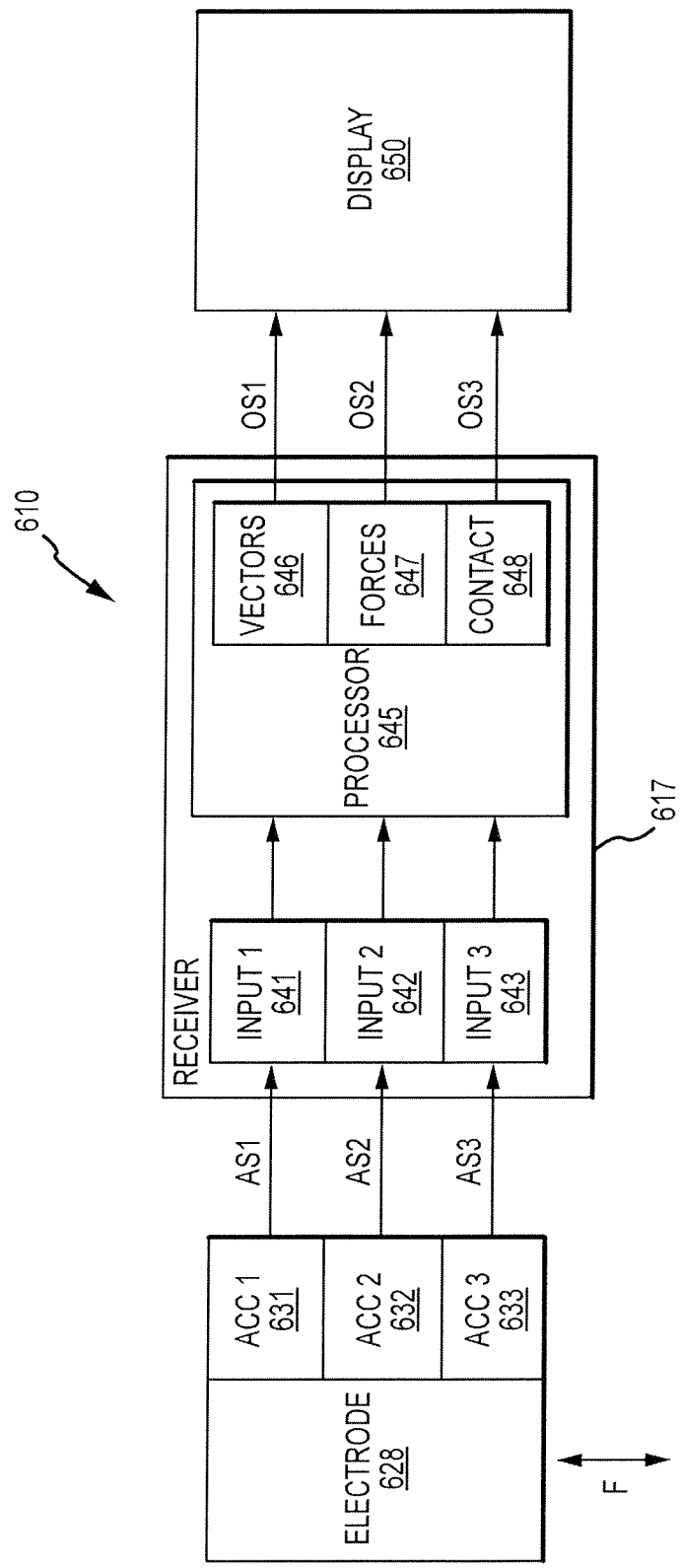
FIG. 6 is a simplified schematic and block diagram view of an accelerometer-based contact sensing system in accordance with the invention.

FIG. 6 is a schematic and block diagram overview of an embodiment of a system 610. The system 610 includes a receiver 617 that is responsive to output signals provided by accelerometers 631, 632, 633, which are configured to detect acceleration of an electrode 628. Receiver 617 includes, among other things, a processor 645 that is configured to process the received signals in a manner described below to produce one or more parameters of interest, such as acceleration, applied force, degree of electrode-to-tissue contact, and the like. The receiver may be further configured to display information, such as the computed parameters of interest, to a user, such as an electrophysiologist, on a display 650.

Accelerometers 631, 632, 633 are coupled to electrode 628. A force F is applied to electrode 628 causing electrode 628 to move. The movement of electrode 628 causes accelerometers 631, 632, 633 to sense acceleration and to output respective acceleration signals AS1, AS2, AS3. Signals AS1, AS2, AS3 are received by a receiver 617 at inputs 641, 642, 643. Inputs 641, 642, 643 are configured to receive acceleration signals AS1, AS2, AS3 and to provide the signals AS1, AS2, AS3 to a processor 645.

Processor 645 may include hardware and/or software configured to receive the acceleration signals AS1, AS2, AS3, and to process the signals AS1, AS2, AS3 to determine one or more of an acceleration vector, force associated with one or more of the acceleration signals AS1, AS2, AS3, a force vector, and whether there is contact between the electrode and a surface, such as a wall of a beating heart. Processor 645 may determine the force acting on electrode 628 by multiplying acceleration values by the mass of electrode 628. Additionally, or alternatively, processor 645 may determine force directly from the sensed acceleration signals using a lookup table or other mechanism. Contact may be determined by analyzing the forces applied to electrode 628. For example, contact with a beating heart may be characterized by repeated acceleration in a first direction followed by acceleration in a second direction. The second direction may be opposite the first direction.

Receiver 617 may be configured to output resultant values, such as acceleration value OS1, Force value OS2, and contact value OS3, to one or more user interface devices, such as a display screen 650. Display screen 650 may be a dedicated screen for providing indications related to receiver outputs OS1, OS2, OS3. Display 650 may also be incorporated into one or more other devices such as an EnSite NavX™ Navigation and Visualization System.

Acceleration signals, such as signals AS1, AS2, AS3, may be used alone or in conjunction with one or more other signals, such as signals from force sensors, temperature sensors, etc., to aid in electrophysiological procedures. For example, using acceleration signals in conjunction with force signals may allow detection of both static and dynamic forces. Acceleration signals may be used, in part, to determine tilt, direction, orientation, or other directional attributes of electrode 28, and may assist in providing a clear picture of electrode 28 interaction with an associated treatment area. Signals may also be used in conjunction with one or more visualization systems to provide a more complete view of a treatment area, such as a cardiac chamber, as well as the position of an electrode, such as electrode 28, relative to the treatment area.

Acceleration signals may be used to determine local health of cardiac tissue, such as by determining the force with which cardiac muscle displaces an electrode 28 in contact therewith. Additionally, signals used to determine contact with tissue may, for example, increase the safety of ablation procedures by ensuring ablation energy is provided to an electrode only when the electrode is in contact with tissue.

In addition to the foregoing, embodiment of the present invention may include catheters including additional features. For example, the present teachings may be included in an irrigated catheter.

Although embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:
1. A method comprising:
providing a catheter having a proximal portion and a flexible distal portion, the proximal portion being stiff relative to the flexible distal portion;

providing an electrode coupled to the flexible distal portion, and an accelerometer coupled to the electrode; and monitoring an output of the accelerometer to recognize when the electrode comes into contact with a tissue surface of an endocardial wall of a heart of the patient, and detecting when the electrode contacts the tissue surface by recognizing, using said accelerometer output, when the electrode motion corresponds to a motion of the tissue surface.

2. The method of claim 1 further comprising:
detecting when the electrode is no longer in contact with the tissue surface.

3. The method of claim 1, wherein monitoring comprises monitoring the output of the accelerometer to further recognize to what degree the electrode is in contact with the tissue surface.

4. The method of claim 1 further comprising generating the accelerometer output as a signal indicative of an acceleration of the electrode when the electrode is subjected to an external applied force thereto by the tissue surface in contact with the electrode.

5. The method of claim 4 wherein said monitoring the output of the accelerometer to recognize when the electrode comes into contact with the tissue surface comprises processing the acceleration indicative signal to produce a first parameter indicative of the applied force experienced by the electrode based on the acceleration indicative signal and further based on an electrode mass associated with the electrode.

6. The method of claim 5 wherein said monitoring the output of the accelerometer to recognize when the electrode comes into contact with the tissue surface further comprises processing at least one of the acceleration indicative signal and the applied force indicative parameter to produce a second parameter that indicates to what degree the electrode is in contact with the tissue surface.

7. The method of claim 6 wherein said monitoring the output of the accelerometer to recognize when the electrode comes into contact with the tissue surface further comprises determining contact by detecting, in accordance with at least the acceleration indicative signal, repeated acceleration in a first direction followed by an acceleration in a second direction opposite of the first direction.

8. The method of claim 5 wherein said monitoring the output of the accelerometer to recognize when the electrode comes into contact with the tissue surface further comprises determining contact when a first force applied to the electrode as indicated by the first parameter is greater than a second force acting on the flexible distal portion of the catheter.

9. The method of claim 4 wherein said monitoring the output of the accelerometer to recognize when the electrode comes into contact with the tissue surface further comprises determining contact when electrode accelerations according to the acceleration indicative signal are contemporaneous with the systole and diastole of a cardiac chamber.

10. The method of claim 6 further comprising outputting to one or more user interface devices an output resultant value selected from the group comprising (i) the acceleration indicative signal; (ii) the first parameter indicative of the force applied to the electrode; and (iii) the second parameter indicative of the degree of contact.

11. The method of claim 10 further comprising outputting a notification indicating that the electrode is no longer in contact with the tissue surface.

12. The method of claim 10 wherein the one or more user interface devices comprise a display screen, wherein outputting the resultant values comprises displaying the resultant values on the display screen.

13. The method of claim 1 wherein providing the catheter further comprises providing a shaft wherein the proximal portion comprises the proximal portion of the shaft and the distal portion comprises the distal portion of the shaft.

14. The method of claim 1 wherein the electrode extends along an axis, said method further comprising positioning the accelerometer to detect the acceleration of the electrode with respect to the axis.

15. The method of claim 1 further comprising a plurality of accelerometers configured to provide respective signals indicative of at least one of a magnitude, an orientation and a directionality of acceleration of the electrode.

16. A method, comprising:
providing a catheter having a proximal portion and a flexible distal portion, the proximal portion being stiff relative to the flexible distal portion;
providing an electrode coupled to the flexible distal portion;
providing a plurality of accelerometers coupled to the electrode; and
monitoring respective outputs of the plurality of accelerometers to recognize when the electrode comes into contact with a tissue surface in a body of a patient by recognizing, using the accelerometer outputs, when the electrode motion corresponds to a motion of the tissue surface.

17. The method of claim 16 further comprising:
detecting when the electrode is no longer in contact with the tissue surface.

18. The method of claim 16, wherein monitoring comprises monitoring the outputs of the accelerometers to further recognize to what degree the electrode is in contact with the tissue surface.

19. The method of claim 16 further comprising generating the accelerometer outputs as respective signals and processing the respective signals to determine at least one of a magnitude and direction of the acceleration of the electrode.

* * * * *